United States Patent
Dagsland et al.

[19]

[11] Patent Number: 6,142,145
[45] Date of Patent: Nov. 7, 2000

[54] INHALATION DEVICE

[75] Inventors: Allan Dagsland, Karlshamn; Karin Malmqvist-Granlund, Kävlinge, both of Sweden; Risto Virtanen, Nurmijärvi, Finland

[73] Assignee: Astra Aktiebolag, Sodertalje, Sweden

[21] Appl. No.: 09/068,379

[22] PCT Filed: Mar. 13, 1998

[86] PCT No.: PCT/SE98/00460

§ 371 Date: May 8, 1998

§ 102(e) Date: May 8, 1998

[87] PCT Pub. No.: WO98/41259

PCT Pub. Date: Sep. 24, 1998

[30] Foreign Application Priority Data

Mar. 14, 1997 [SE] Sweden .................................. 9700940

[51] Int. Cl.$^7$ .......................... A61M 15/00; A61M 16/00; B05D 7/14; B05D 83/06
[52] U.S. Cl. ................................. 128/203.15; 128/203.23
[58] Field of Search .................... 128/203.12, 213.15, 128/203.23, 203.24; 604/58

[56] References Cited

U.S. PATENT DOCUMENTS

| | | | |
|---|---|---|---|
| 2,603,216 | 7/1952 | Taplin et al. ........................ | 128/203.15 |
| 2,672,865 | 3/1954 | Willis ................................. | 128/203.15 |
| 3,948,264 | 4/1976 | Wilke et al. . | |
| 4,668,218 | 5/1987 | Virtanen ................................. | 604/58 |
| 4,907,583 | 3/1990 | Wetterlin et al. ..................... | 128/203.15 |
| 5,243,970 | 9/1993 | Ambrosio et al. .................... | 128/203.15 |
| 5,327,883 | 7/1994 | Williams et al. ..................... | 128/203.12 |
| 5,331,953 | 7/1994 | Andersson et al. ................... | 128/200.14 |
| 5,429,122 | 7/1995 | Zanen et al. ......................... | 128/203.15 |
| 5,435,297 | 7/1995 | Klein . | |
| 5,549,101 | 8/1996 | Trofast et al. ....................... | 128/203.15 |
| 5,687,710 | 11/1997 | Ambrosio et al. .................... | 128/203.15 |
| 5,699,789 | 12/1997 | Hendricks ............................ | 128/203.15 |
| 5,740,792 | 4/1998 | Ashley et al. ....................... | 128/203.15 |
| 5,765,552 | 6/1998 | Zanen et al. ......................... | 128/203.15 |
| 5,829,434 | 11/1998 | Ambrosio et al. .................... | 128/203.15 |

FOREIGN PATENT DOCUMENTS

| | | |
|---|---|---|
| 0237507 | 9/1987 | European Pat. Off. . |
| 0547429 | 6/1993 | European Pat. Off. . |
| WO 92/04928 | 4/1992 | WIPO . |
| WO92/10228 | 6/1992 | WIPO . |
| WO 94/14492 | 7/1994 | WIPO . |
| WO95/28192 | 10/1995 | WIPO . |
| WO 97/00703 | 1/1997 | WIPO . |

OTHER PUBLICATIONS

International Search Report, PCT/SE 98/00460, Jul. 30, 1998.

Primary Examiner—John G. Weiss
Assistant Examiner—Joseph F. Weiss
Attorney, Agent, or Firm—Fish & Richardson P.C.

[57] ABSTRACT

An inhaler for administering powder by inhalation, including an inhaler body having two ends and a peripheral wall therebetween; an inhalation unit disposed in the inhaler body, the inhalation unit comprising an inhalation channel, the inhalation channel having an air inlet and an outlet; a dosing unit disposed in the inhaler body for providing a dose of powder to the inhalation channel such that a stream of air containing powder may be drawn from the outlet of the inhalation channel on inhalation by a user; a divider having a first surface bounded by a periphery and which substantially closes one end of the inhaler body; a mouthpiece attached to the periphery of the divider, the mouthpiece having a substantially radially directed flange which provides a second surface and which, together with the first surface, defines an air chamber; a first inlet for the air chamber provided in the first surface within the periphery of the divider and in fluid communication with the outlet of the inhalation channel; a second inlet for the air chamber disposed in the first surface within the periphery of the divider and adjacent the first inlet, a stream of supplementary air in use being drawn through the second inlet on inhalation by the user; and a discrete opening in peripheral wall of the inhaler body which is in fluid communication with the second inlet of the air chamber.

27 Claims, 6 Drawing Sheets

INHALATION DEVICE

This is a 371 of International Patent Application No. PCT/SE98/00460, with an international filing date of Mar. 13, 1998, now pending.

The present invention relates to a powder inhaler for administering powder by inhalation.

A number of powder inhalers are known which use different systems for introducing a dose of powder into an air stream. Typically, the powder is inhaled into the lungs of a patient in order to treat, for example, asthma.

EP-A-0237507 discloses one such powder inhaler. This inhaler comprises an inhalation channel and a mouthpiece which includes an air chamber and an outlet nozzle, through which a stream of air is drawn during inhalation by a user, and a dosing mechanism for providing a dose of powder to the inhalation channel. During inhalation, air is first drawn into and through the inhalation channel so as to pick up powder. The stream of air containing powder is then drawn through the air chamber and out of the outlet nozzle of the mouthpiece.

FIG. 1 illustrates such a powder inhaler. The inhaler comprises a mouthpiece 2 which includes an outlet nozzle 4, an inhaler body 6 and a rotatable grip portion 8 for operating a dosing mechanism for providing doses of powder for inhalation. The inhaler body 6 is provided with an opening 10 which is filled with a window 12 through which an indicating wheel 42 is visible so as to provide an indication as to the usage of the inhaler.

FIG. 2 illustrates in exploded view component parts disposed within and to the inhaler body 6. The inhaler body 6 is capped with a divider 14 which is fixed thereto. For aesthetic reasons the inhaler body 6 is an opaque moulding. The divider 14 is a transparent moulding which has a depending tongue 15, a part of which forms the window 12.

Within the inhaler body 6 are housed the component parts of the dosing mechanism. These component parts include a dosing unit 16 which comprises a member 17 having a planar surface in which a plurality of dosing elements 18 are provided and a shaft 20 which extends axially from the centre of the member 17, an inhalation unit 22 which comprises an inhalation channel 24 and a storage unit 26 which comprises a storage chamber 28 for storing powder. The above-mentioned component parts of the dosing mechanism are assembled by passing the inhalation channel 24 through an opening 30 in the storage unit 26 and passing the shaft 20 through central openings 32, 34 in the inhalation unit 22 and the storage unit 26 respectively. When so assembled, the upper ends of the inhalation channel 24 and the storage chamber 28 pass respectively through first and second openings 36, 38 in the divider 14. In this way, the inhalation unit 22 and the storage unit 26 are fixed in position in relation to one another and the dosing unit 16 can be rotated relative thereto.

In this inhaler the storage unit 28 is open at the bottom such that in use powder is provided to the dosing unit 16 under the action of gravity and the inhalation unit 22 further comprises scrapers 40 which are resiliently biased against the surface of the member 17 in which the dosing elements 18 are provided. In this way, as the dosing unit 16 is rotated, the dosing elements 18 are filled with powder by the scrapers 40. Powder is prevented from passing through the dosing elements 18 by a plate (not illustrated) which is disposed beneath the dosing unit 16.

As illustrated in FIG. 2, the divider 14 further comprises a supporting member 41 for rotatably supporting an indicating wheel 42. The indicating wheel 42 includes a plurality of teeth 44 disposed around the periphery thereof which engage with a spiral groove or protrusion 46 on the end face of the shaft 20. The supporting member 41 is configured to align the indicating wheel 42 such that a part of the periphery thereof is disposed adjacent the inner surface of the window 12. In use, as the dosing unit 16 is rotated, the spiral groove or protrusion 46 engages with one or more of the teeth 44 on the indicating wheel 42 so as to rotate the same. In this way, by providing a coloured marking on the periphery of the indicating wheel 42, it is possible to provide the user with a visible indication at the window 12 as to the usage of the inhaler.

As illustrated in FIG. 5, the mouthpiece 2 is fixed to the divider 14. The mouthpiece 2 comprises first and second parts 48, 50, the first part 48 being the outer part which is gripped by the lips of a user and the second part 50 being an insert fitted within the first part 48. The second part 50 comprises a tubular section 52, which includes one or more spirally or helically shaped projections 54 that act to deflect the air drawn therethrough and thereby deagglomerate any larger particles of entrained powder, and a substantially radially-directed flange 56, which provides a surface that together with the upper surface of the divider 14 defines an air chamber 58 that is in fluid communication with the inhalation channel 24 through which air containing powder is drawn on inhalation by a user. Within the air chamber 58, the air flow is to a certain extent turbulent. By providing a turbulent flow, both the deagglomeration and the distribution of the powder in the stream of air are improved.

In use, as described hereinabove, powder is transferred from the storage chamber 28 to one of the dosing elements 18, and, with rotation of the dosing unit 16, the one dosing element 18 provides a dose of powder to the inhalation channel 24. The dosing unit 16 is rotated by rotating the grip portion 8 in one sense, in this inhaler the counter-clockwise sense when viewed from above, between first and second angularly-spaced positions. For this purpose the dosing unit 16 comprises wedge-shaped elements 60 disposed around the periphery of the member 17 and the grip portion 8 comprises a resilient member (not illustrated) which is configured to engage with an axially-directed surface 60a of a respective one of the wedge-shaped elements 60 so as to rotate the dosing unit 16 by pushing the respective wedge-shaped element 60. On rotation of the grip portion 8 in the opposite, clockwise sense between the second and the first angularly-spaced positions, the dosing unit 16 remains stationary and the resilient member is located behind the axially-directed surface 60a of the adjacent wedge-shaped element 60; the resilient member riding over an inclined surface 60b of the adjacent wedge-shaped element 60.

WO-A-94/14492 discloses a powder inhaler for administering powder by inhalation. This inhaler comprises a metering plate, which includes a metering hole for holding a metered dose of powder, and an inhalation channel, one end of which is open and defines an inlet which in use is located over the metering hole in the metering plate such that on inhalation by a user the metered dose of powder is drawn through the inhalation channel.

It is an aim of the present invention to provide a powder inhaler which provides both for improved deagglomeration and distribution of powder in inhaled air as compared to the above-described known powder inhalers.

Accordingly, the present invention provides an inhaler for administering powder by inhalation, comprising: an inhaler body; an inhalation unit disposed in the inhaler body, the inhalation unit comprising an inhalation channel which includes an inlet and an outlet through which a stream of air containing powder is in use drawn on inhalation by a user; a dosing unit for providing a dose of powder to the inhalation channel disposed in the inhaler body; and an air chamber which includes a first inlet in fluid communication with the outlet of the inhalation channel and a second inlet disposed adjacent the first inlet thereof through which a stream of supplementary air is in use drawn on inhalation by the user; characterized in that the inlet of the inhalation channel is disposed in a lateral wall thereof.

Preferably, the first and second inlets of the air chamber are disposed in substantially the same plane.

In one embodiment the first and second inlets of the air chamber are provided in first and second separate openings in a surface defining the air chamber.

Preferably, the first and second openings are spaced by a distance equivalent to the internal dimension of the outlet of the inhalation channel.

More preferably, the first and second openings are spaced by a distance equivalent to half of the internal dimension of the outlet of the inhalation channel.

Still more preferably, the first and second openings are spaced by a distance equivalent to one-quarter of the internal dimension of the outlet of the inhalation channel.

In another embodiment the first and second inlets of the air chamber are provided in a single opening in a surface defining the air chamber.

Preferably, the outlet of the inhalation channel extends to the single opening, with the outlet of the inhalation channel defining the first inlet of the air chamber and a space between the outer surface of the inhalation channel and the periphery of the single opening defining the second inlet of the air chamber.

More preferably, the inhalation channel and the single opening are configured such that the space surrounds the outer surface of the inhalation channel.

Preferably, the air chamber comprises only one inlet through which supplementary air can be drawn.

Preferably, the inhaler further comprises a divider which substantially closes one end of the inhaler body, the divider defining a surface of the air chamber in which the first and second inlets thereof are provided.

Preferably, the inhaler body and the divider are formed as a single integral unit.

Preferably, the inhaler further comprises a mouthpiece attached to the periphery of the divider, the mouthpiece and the divider defining the air chamber.

Preferably, the inhaler further comprises an indicating wheel for providing an indication as to the usage of the inhaler disposed in the inhaler body so as to be rotatable within a diametrical plane containing the central axis thereof, the inhaler body including an opening through which at least a part of the indicating wheel is visible.

Preferably, the inhaler further comprises a storage unit disposed in the inhaler body, the storage unit comprising a storage chamber for storing powder.

More preferably, the inhalation unit and the storage unit are formed as a single integral unit.

Preferably, the storage unit is formed of a transparent material and further comprises a portion which substantially fills the opening through which at least a part of the indicating wheel is visible.

In one embodiment the storage unit further comprises a supporting member for rotatably supporting the indicating wheel.

In another embodiment the divider comprises a supporting member for rotatably supporting the indicating wheel.

Preferably, the inhaler body includes an opening which is in fluid communication with the second inlet of the air chamber.

Preferably, the inhaler body includes an opening which is in fluid communication with the inlet of the inhalation channel.

In one embodiment the inhaler body includes a recess, one of the surfaces of which includes an opening which is in fluid communication with the second inlet of the air chamber.

Preferably, one of the surfaces of the recess includes an opening which is in fluid communication with the inlet of the inhalation channel.

Preferably, one of the surfaces of the recess includes the opening through which at least a part of the indicating wheel is visible.

In another embodiment the inhaler body includes a recess, one of the surfaces of which includes an opening which is in fluid communication with the inlet of the inhalation channel.

Preferably, one of the surfaces of the recess includes the opening through which at least a part of the indicating wheel is visible.

In a further embodiment the inhaler body includes a recess comprising first and second opposing surfaces which are substantially parallel to the major surface of the divider and at least first and second side surfaces joining the first and second opposing surfaces, the opposing surface proximate the divider including an opening in fluid communication with the second inlet of the air chamber, the other opposing surface including an opening in fluid communication with the inlet of the inhalation channel and one of the side surfaces including the opening through which at least a part of the indicating wheel is visible.

Preferably, the inhaler body is substantially cylindrical.

In the inhaler of the present invention the stream of air containing powder drawn through the first inlet of the air chamber from the outlet of the inhalation channel is disturbed by the stream of supplementary air drawn through the second inlet of the air chamber. The two streams of air are sufficiently close to interact with one another, thereby causing additional turbulence and assisting in deagglomerating and distributing the powder.

Medicaments suitable for administration by the powder inhaler of the present invention are any which may be delivered by inhalation and include, for example, β2-adrenoreceptor agonists, for example, salbutamol, terbutaline, rimiterol, fenoterol, reproterol, adrenaline, pirbuterol, isoprenaline, orciprenaline, bitolterol, salmeterol, formoterol, clenbuterol, procaterol, broxaterol, picumeterol, TA-2005, mabuterol and the like, and their pharmacologically acceptable esters and salts; anticholinergic bronchodilators, for example, ipratropium bromide and the like; glucocorticosteroids, for example, beclomethasone, fluticasone, budesonide, tipredane, dexamethasone, betamethasone, fluocinolone, triamcinolone acetonide, mometasone and the like, and their pharmacologically acceptable esters and salts; antiallergic medicaments, for example, sodium cromoglycate and nedocromil sodium; expectorants; mucolytics; antihistamines; cyclooxygenase inhibitors; leukotriene synthesis inhibitors; leukotriene antagonists; phospholipase-A2 (PLA2) inhibitors; platelet aggregating factor (PAF) antagonists and prophylactics of asthma; antiarrhythmic medicaments; tranquilisers; cardiac glycosides; hormones; antihypertensive medicaments; antidiabetic medicaments; antiparasitic medicaments; anticancer medicaments; sedatives; analgesic medicaments; antibiotics; antirheumatic medicaments; immunotherapies; antifungal medicaments; antihypotension medicaments; vaccines; antiviral medicaments; proteins; polypeptides and peptides, for example, peptide hormones and growth factors; polypeptide vaccines; enzymes; endorphines; lipoproteins and polypeptides involved in the blood coagulation cascade; vitamins; and others, for example, cell surface receptor blockers, antioxidants, free radical scavengers and organic salts of N,N'-diacetylcystine.

Preferred embodiments of the present invention will now be described hereinbelow by way of example only with reference to the accompanying drawings, in which.

Structurally, the powder inhalers in accordance with the preferred embodiments of the present invention have many features in common with the above-described first known powder inhaler. For this reason, and in order to avoid unnecessary duplication of description, only the structural differences will be described in detail and reference is made to the preceding description of the known powder inhaler.

Figure 1:
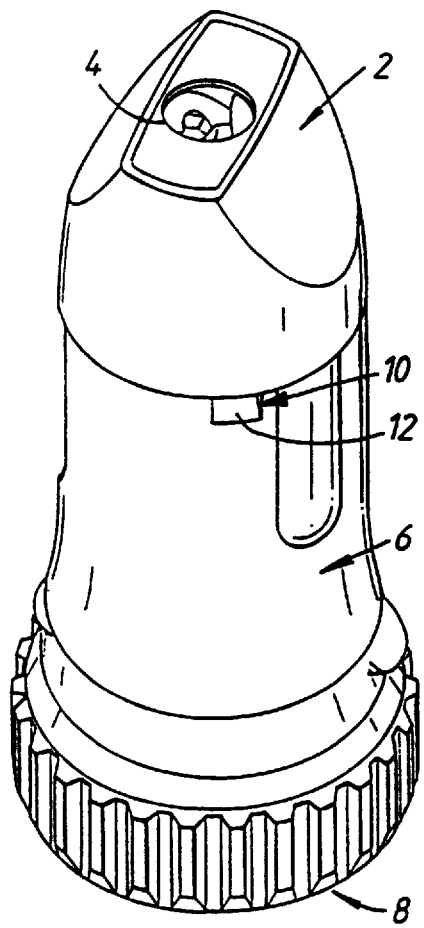
FIG. 1 illustrates a perspective view of a known powder inhaler.
Figure 2:
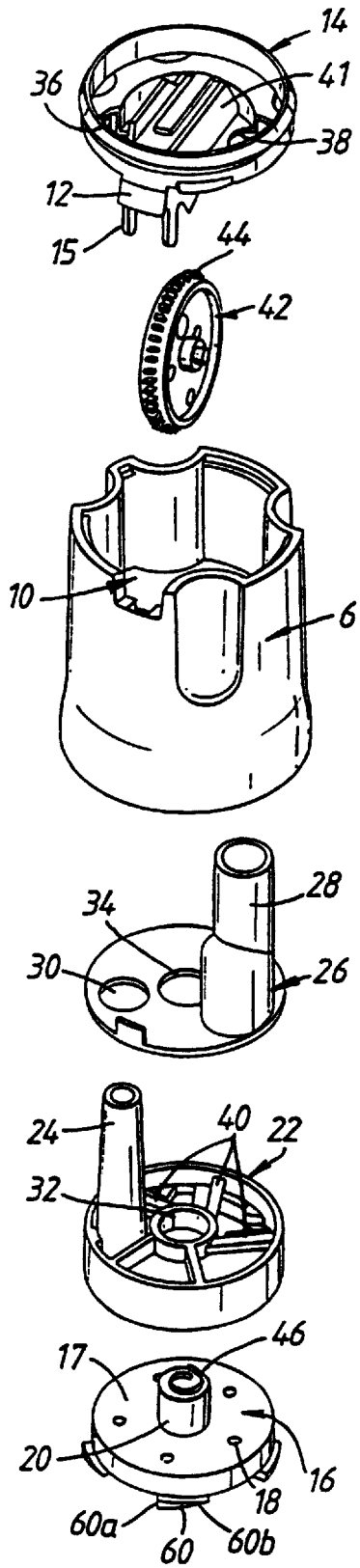
FIG. 2 illustrates an exploded perspective view of component parts of the inhaler of FIG. 1.
Figure 3:
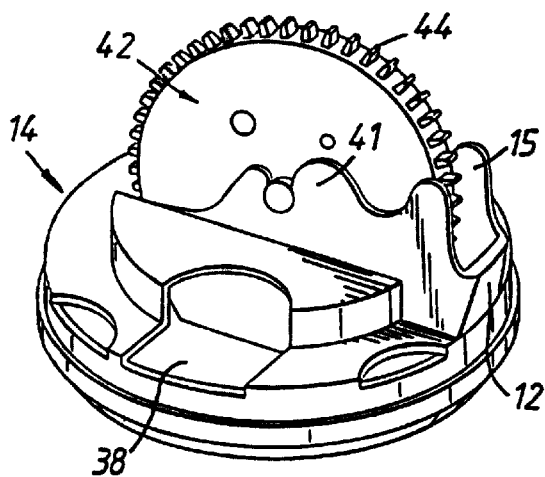
FIG. 3 illustrates component parts of the inhaler of FIG. 1.
Figure 5:
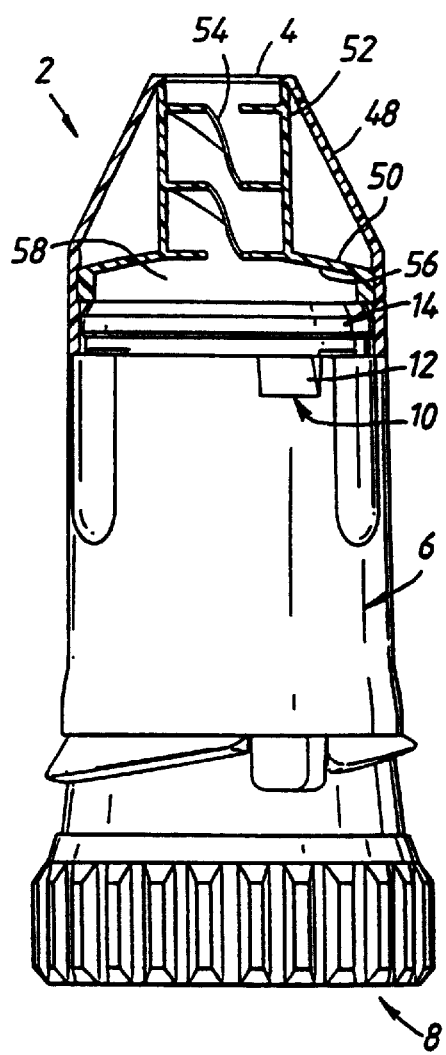
FIG. 5 illustrates a part-sectional side view of the inhaler of FIG. 1.
Figure 4:
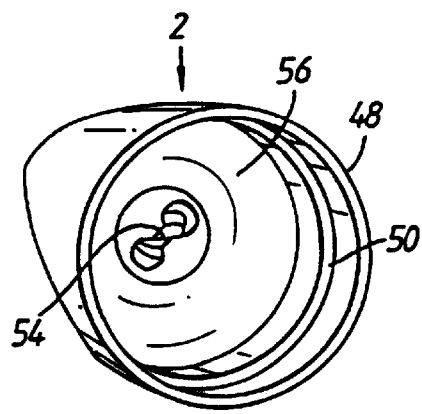
FIG. 4 illustrates the underside of the mouthpiece of the inhaler of FIG. 1.
Figure 6:
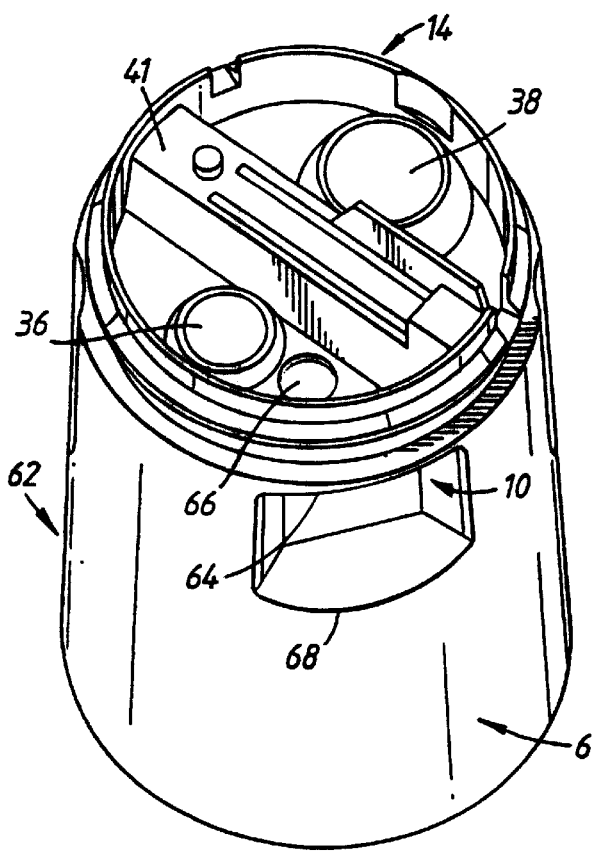
FIGS. 6 and 7 illustrate component parts of a powder inhaler in accordance with a first embodiment of the present invention.
Figure 7:
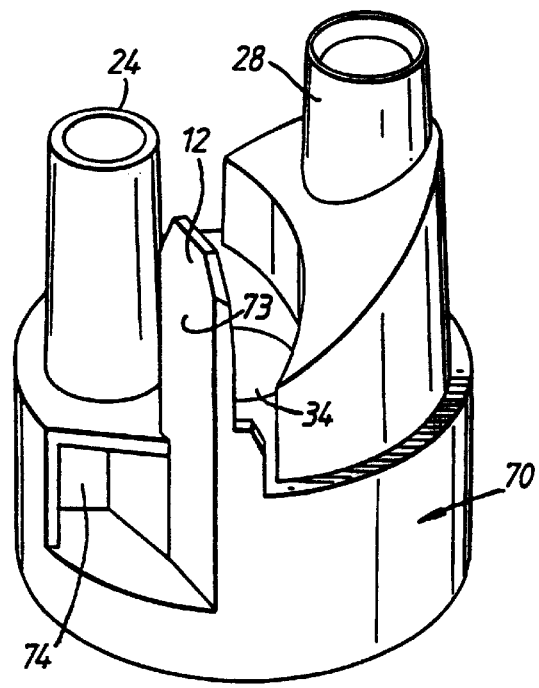

FIGS. 6 and 7 illustrate respectively a body part 62 and a structural unit 70 of a powder inhaler in accordance with a first embodiment of the present invention. This inhaler is a modification of the above-described known powder inhaler.

This inhaler differs from the above-described known powder inhaler in that the inhaler body 6 and the divider 14 are provided by a body part 62 which is a single part moulded from an opaque material. As in the above-described known powder inhaler, the inhaler body 6 includes the opening 10 through which the indicating wheel 42 is visible.

This inhaler further differs from the above-described known powder inhaler in that the inhaler body 6 includes a further opening 64 in the peripheral wall thereof and the divider 14 includes a further opening 66 juxtaposed the first opening 36 therein into which the inhalation channel 24 extends. The further opening 66 in the divider 14 is in fluid communication with the further opening 64 in the peripheral wall of the inhaler body 6 and acts as a supplementary air inlet, whereby, during inhalation, supplementary air is drawn through the further opening 66 and into the air chamber 58. Owing to the close proximity of the further opening 66 to the first opening 36 into which the inhalation channel 24 extends, the stream of supplementary air drawn through the further opening 66 induces turbulence in the stream of air containing powder drawn through the first opening 36 and consequently improves both the distribution of the entrained powder and the deagglomeration of powder agglomerates. In this embodiment the inhaler body 6 includes a recess 68 in side surfaces of which are provided the opening 10 through which the indicating wheel 42 is visible and the further opening 64 which is in fluid communication with the further opening 66 in the divider 14. The recess 68 is located such that the opening 10 is adjacent one of the side surfaces of the indicating wheel 42. In an alternative embodiment the further opening 64 could be provided in another surface of the recess 68, for example, in the upper surface of the recess 68 proximate the further opening 66.

This inhaler yet further differs from the above-described known powder inhaler in that the side surface of the indicating wheel 42 adjacent the opening 10 includes an indication or indications representative of the usage of the inhaler.

Figure 8:
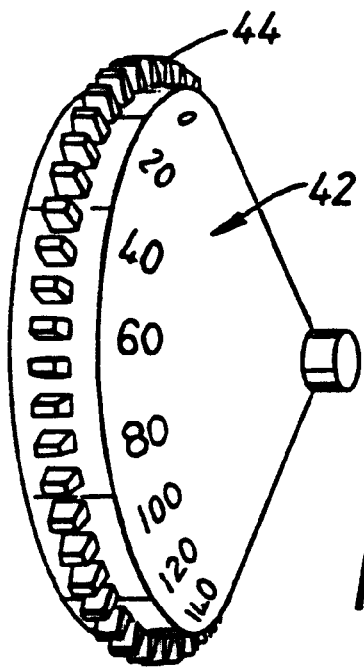
FIGS. 8 and 9 illustrate indicating wheels for use with the powder inhaler of FIGS. 6 and 7.
Figure 9:
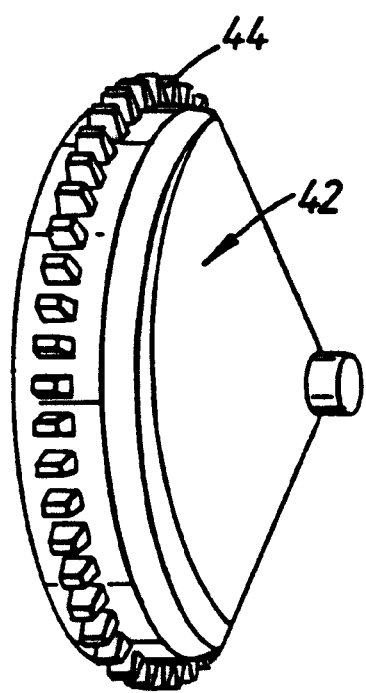

In one embodiment the indicating wheel 42 can be provided with numeric indications of increasing or decreasing value for indicating the number of times the inhaler has been operated or the number of times the inhaler may still be operated. In another embodiment the indicating wheel 42 may alternatively, or additionally, be provided with a circumferential band of changing width along its length, such that the width visible through the window 12 is representative of the number of doses delivered. Colour changes may also be used to indicate the number of doses delivered or remaining. Such colour changes may be applied in conjunction with the indications described hereinabove. For instance, by using numerals of different colour, or by using a band, the colour of which changes along its length. In a preferred embodiment, in order to assist viewing, the side surface of the indicating wheel 42 adjacent the window 12 can be formed as a conical surface, with the surface of the cone enclosing an angle of from 10° to 30°, preferably about 15°, with the rotational plane of the indicating wheel 42. FIGS. 8 and 9 illustrate preferred indicating wheels 42.

In this embodiment the recess 68 is configured such that the side surface thereof in which the opening 10 is provided is parallel to the adjacent side surface of the indicating wheel 42. It will be appreciated, however, that, for the purposes of viewing the indicating wheel 42, it is sufficient that the opening 10 has a radial component. It will also be appreciated that the recess 68 can have any shape which allows a user to view the adjacent side surface of the indicating wheel 42 through the opening 10.

This inhaler still further differs from the above-described known powder inhaler in that the inhalation unit 22 and the storage unit 26 are provided by a structural unit 70 which is a single part moulded from a transparent material and comprises a tongue 73, one part, in this embodiment the distal end, of which is shaped and dimensioned such that when the structural unit 70 is fitted in the inhaler body 6 that part of the tongue 73 fills the opening 10 so as to provide the window 12. As in the above-described known powder inhaler, the indicating wheel 42 is rotatably supported to the underside of the divider 14.

This inhaler still yet further differs from the above-described known powder inhaler in that the lower end of the inhalation channel 24 is provided with a lateral opening 74 through which air is drawn on inhalation by a user.

Figure 10:
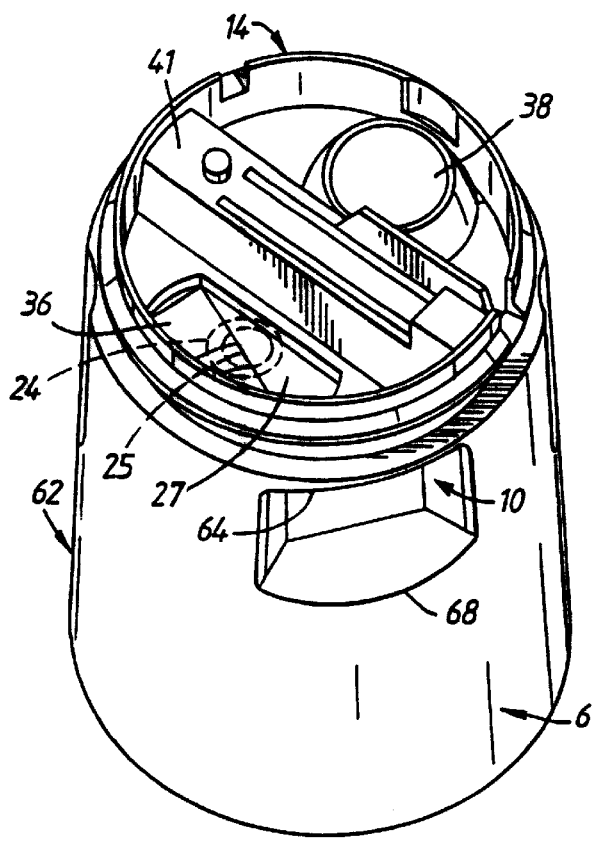
FIG. 10 illustrates a component part of a powder inhaler in accordance with a second embodiment of the present invention.

FIG. 10 illustrates a body part 62 of a powder inhaler in accordance with a second embodiment of the present invention. This inhaler is a modification of the inhaler of the above-described first embodiment.

This inhaler differs from the inhaler of the above-described first embodiment in that the first opening 36 into which the upper end of the inhalation channel (shown in phantom in FIG. 10) 24 extends is, which terminates with outlet 25, of greater dimension than the outer dimension of the inhalation channel 24. This construction thus provides an opening about the outer periphery of the inhalation channel 24 which is in fluid communication with the opening 64 in the recess 68. In this way, in a similar manner to the inhaler of the above-described first embodiment, the stream of supplementary air drawn through the opening about the outer periphery of the inhalation channel 24 induces turbulence in the stream of air containing powder drawn through the inhalation channel 24, which turbulence improves both the distribution and the deagglomeration of the powder.

Figure 11:
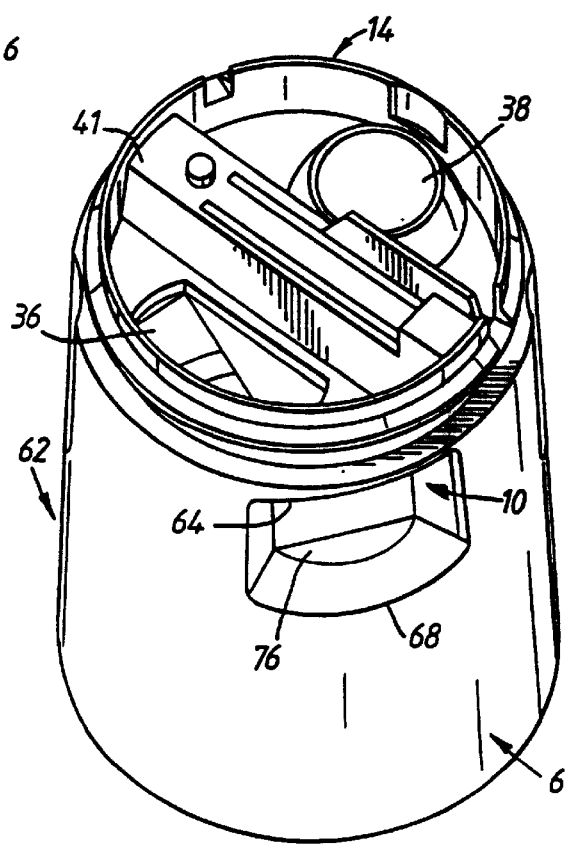
FIG. 11 illustrates a component part of a powder inhaler in accordance with a third embodiment of the present invention.

FIG. 11 illustrates a body part 62 of a powder inhaler in accordance with a third embodiment of the present invention. This inhaler is a modification of the inhaler of the above-described second embodiment.

This inhaler differs from the inhaler of the above-described second embodiment in that the opening 64 in the recess 68, which is in fluid communication with the supplementary air inlet provided by the opening about the outer periphery of the inhalation channel 24, is located in the upper surface of the recess 68 and in that the lower surface of the recess 68 is partially cut away to provide an opening 76 into the inhaler body 6 which is in fluid communication with the lateral opening 74 in the inhalation channel 24. During inhalation by a user, air is drawn through both of the openings 64, 76 in the recess 68, with the air drawn through the opening 64 in the upper surface of the recess 68 being drawn through the supplementary air inlet provided by the opening in the divider 14 about the outer periphery of the inhalation channel 24 and the air drawn through the opening 76 in the lower surface of the recess 68 being drawn through the lateral opening 74 in the inhalation channel 24.

Figure 12:
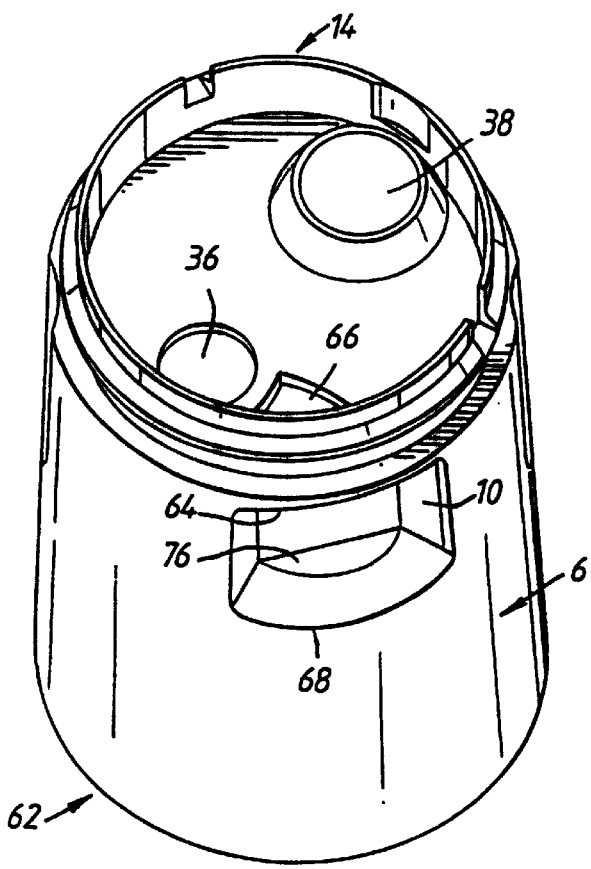
FIGS. 12 and 13 illustrate component parts of a powder inhaler in accordance with a fourth embodiment of the present invention.
Figure 13:
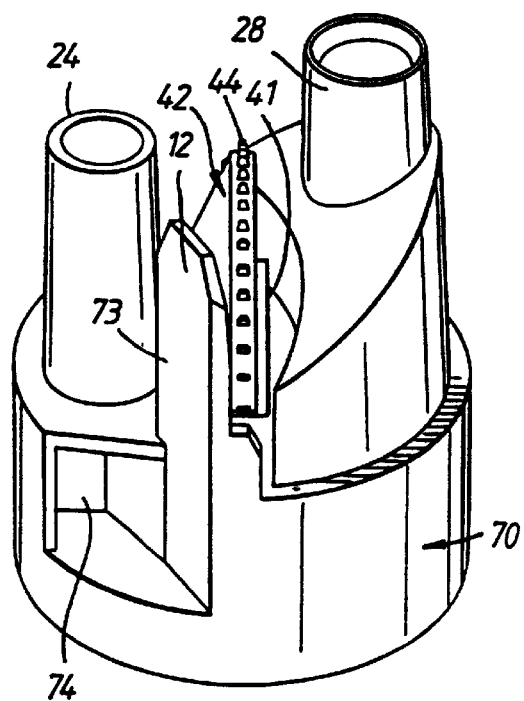

FIGS. 12 and 13 illustrate respectively a body part 62 and a structural unit 70 of a powder inhaler in accordance with a fourth embodiment of the present invention. This embodiment is a modification of the inhaler of the above-described third embodiment.

This inhaler differs from the inhaler of the above-described third embodiment in that the structural unit 70 includes the supporting member 41 for rotatably supporting the indicating wheel 42 instead of the divider 14.

This inhaler further differs from the inhaler of the above-described third embodiment in that the divider 14 is formed with a substantially flat top surface and includes a separate further opening 66, similarly to the inhaler of the above-described first embodiment, which acts as a supplementary air inlet. In this way, the risk of powder accumulating at this top surface is minimized. This is of particular importance where the top surface of the divider 14 forms the lower wall of the air chamber 58.

In each of the above-described embodiments the storage chamber 28 is crescent-shaped in plan view and thereby provides an increased storage capacity. It will be understood, however, that the storage chamber 28 may be formed as a cylinder as in the above-described known powder inhaler.

Finally, it will be understood by a person skilled in the art that the present invention is not limited to the described embodiments but can be modified in many different ways without departing from the scope of the invention as defined by the appended claims.

What is claimed is:

1. An inhaler for administering powder by inhalation, comprising:

an inhaler body having two ends and a peripheral wall therebetween;

an inhalation unit disposed in the inhaler body, the inhalation unit comprising an inhalation channel, the inhalation channel having an air inlet and an outlet;

a dosing unit disposed in the inhaler body for providing a dose of powder to the inhalation channel such that a stream of air containing powder may be drawn from the outlet of the inhalation channel on inhalation by a user;

a divider having a first surface bounded by a periphery and which substantially closes one end of the inhaler body;

a mouthpiece attached to the periphery of the divider, the mouthpiece having a substantially radially directed flange which provides a second surface and which, together with the first surface, defines an air chamber;

a first inlet for the air chamber provided in the first surface within the periphery of the divider and in fluid communication with the outlet of the inhalation channel;

a second inlet for the air chamber disposed in the first surface within the periphery of the divider and adjacent the first inlet, a stream of supplementary air in use being drawn through the second inlet on inhalation by the user; and a discrete opening in peripheral wall of the inhaler body which is in fluid communication with the second inlet of the air chamber.

2. The inhaler according to claim 1, wherein the first and second inlets of the air chamber are disposed in substantially the same plane.

3. The inhaler according to claim 2, wherein the first and second inlets of the air chamber are provided in first and second separate openings in the first surface of the divider.

4. The inhaler according to claim 3, wherein the first and second openings inlets are spaced by a distance equivalent to the internal diameter of the outlet of the inhalation channel.

5. The inhaler according to claim 3, wherein the first and second openings inlets are spaced by a distance equivalent to half of the internal diameter of the outlet of the inhalation channel.

6. The inhaler according to claim 3, wherein the first and second inlets are spaced by a distance equivalent to one-quarter of the internal diameter of the outlet of the inhalation channel.

7. The inhaler according to claim 1, wherein the first and second inlets of the air chamber are provided in a single opening in the divider.

8. The inhaler according to claim 7, wherein the outlet of the inhalation channel extends to the single opening, with the outlet of the inhalation channel defining the first inlet of the air chamber and a space between the outer surface of the inhalation channel and the periphery of the single opening defining the second inlet of the air chamber.

9. The inhaler according to claim 8, wherein the inhalation channel and the single opening are configured such that the space surrounds the outer surface of the inhalation channel.

10. The inhaler according to any of claim 1, wherein the air chamber includes only one inlet through which supplementary air can be drawn.

11. The inhaler according to claim 1, wherein the inhaler body and the divider are formed as a single integral unit.

12. The inhaler according to any of claim 1, further comprising an indicating wheel disposed in the inhaler body for providing an indicating as to the usage of the inhaler, the inhaler body having a central axis substantially parallel to the inhalation channel, the indicator wheel being rotatable within a diametrical plane containing the central axis thereof and the inhaler body including an opening through which at least a part of the indicating wheel is visible.

13. The inhaler according to claim 12, wherein the inhaler body includes a recess, one of the surfaces of which includes the discrete opening which is in fluid communication with the second inlet of the air chamber and wherein one of the surfaces of the recess includes the opening through which at least a part of the indicating wheel is visible.

14. The inhaler according to claim 12, wherein the inhaler body includes a recess comprising first and second opposing surfaces which are substantially parallel to the major surface of the divider and at least first and second side surfaces joining the first and second opposing surfaces, the opposing surface proximate the divider including an opening in fluid communication with the second inlet of the air chamber, the other opposing surface including an opening in fluid communication with the inlet of the inhalation channel and one of the side surfaces including the opening through which at least a part of the indicating wheel is visible.

15. The inhaler according to claim 12, further comprising a storage unit disposed in the inhaler body, the storage unit comprising a storage chamber for storing powder.

16. The inhaler according to claim 15, wherein the inhalation unit and the storage unit are formed as a single integral unit.

17. The inhaler according to claim 15, wherein the storage unit is formed of a transparent material and further comprises a portion which substantially fills the opening through which at least a part of the indicating wheel is visible.

18. The inhaler according to claim 15, wherein the storage unit comprises a supporting member for rotatably supporting the indicating wheel.

19. The inhaler according to claim 15, wherein the divider comprises a supporting member for rotatably supporting the indicating wheel.

20. The inhaler according to claim 1, wherein the inhaler body includes an opening which is in fluid communication with the inlet of the inhalation channel.

21. The inhaler according to claim 1, wherein the inhaler body includes a recess, one of the surfaces of which includes the discrete opening which is in fluid communication with the second inlet of the air chamber.

22. The inhaler according to claim 1, wherein one of the surfaces of the recess includes an opening which is in fluid communication with the inlet of the inhalation channel.

23. The inhaler according to claim 1 further comprising a storage unit disposed in the inhaler body, the storage unit comprising a storage chamber for storing powder.

24. The inhaler according to claim 1 wherein the inhaler body includes a recess in the peripheral wall formed by a plurality of adjoining surfaces, one of the adjoining surfaces of which includes an opening which is in fluid communication with the inlet of the inhalation channel.

25. The inhaler according to any of claims 1 to 19, wherein the inhaler body includes a recess in the peripheral wall formed by a plurality of adjoining surfaces, one of the adjoining surfaces of which includes an opening which is in fluid communication with the inlet of the inhalation channel.

26. The inhaler according to claim 25, wherein one of the adjoining surfaces of the recess includes the opening through which at least a part of the indicating wheel is visible.

27. The inhaler according to any of claims 1 to 14, wherein the inhaler body is substantially cylindrical.

* * * * *